(12) United States Patent
Church

(10) Patent No.: US 12,067,434 B2
(45) Date of Patent: *Aug. 20, 2024

(54) METHODS OF STORING INFORMATION USING NUCLEIC ACIDS

(71) Applicant: President and Fellows of Harvard College, Cambridge, MA (US)

(72) Inventor: George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/047,328

(22) Filed: Oct. 18, 2022

(65) Prior Publication Data

US 2024/0070422 A1 Feb. 29, 2024

Related U.S. Application Data

(63) Continuation of application No. 17/235,196, filed on Apr. 20, 2021, which is a continuation of application No. 16/590,809, filed on Oct. 2, 2019, now abandoned, which is a continuation of application No. 15/970,257, filed on May 3, 2018, now Pat. No. 10,460,220, which is a continuation of application No. 15/175,430, filed on Jun. 7, 2016, now Pat. No.

(Continued)

(51) Int. Cl.
*C12Q 1/68* (2018.01)
*G06K 19/00* (2006.01)
*G06K 19/02* (2006.01)
*G06N 3/123* (2023.01)
*G16B 30/00* (2019.01)
*G16B 30/20* (2019.01)

(52) U.S. Cl.
CPC ............ *G06K 19/022* (2013.01); *C12Q 1/68* (2013.01); *G06K 19/00* (2013.01); *G06N 3/123* (2013.01); *G16B 30/00* (2019.02); *G16B 30/20* (2019.02)

(58) Field of Classification Search
CPC ........ G06K 19/022; G06K 19/00; C12Q 1/68; G06N 3/123; G16B 30/00
See application file for complete search history.

(56) References Cited

U.S. PATENT DOCUMENTS 6,312,911 B1 11/2001 Bancroft et al.
2003/0044781 A1 3/2003 Korlach et al.
(Continued)

FOREIGN PATENT DOCUMENTS

CN 1177008 A 3/1998
CN 1526015 A 9/2004
(Continued)

OTHER PUBLICATIONS

C. Bancroft: "Long-Term Storage of Information in DNA". Science. vol. 293. No. 5536. Sep. 7, 2001 (Sep. 7, 2001). pp. 1763c-1765. XP055082597. ISSN: 0036-8075. DOI: 10.1126jscience.293.5536. 1763c the whole document.

(Continued)

*Primary Examiner* — Jamara A Franklin
(74) *Attorney, Agent, or Firm* — Banner & Witcoff, Ltd.

(57) ABSTRACT

The present invention relates to methods of synthesizing de novo a polynucleotide storing data using a programmable template independent polymerase.

18 Claims, 2 Drawing Sheets
(2 of 2 Drawing Sheet(s) Filed in Color)
Specification includes a Sequence Listing.

Related U.S. Application Data 9,996,778, which is a continuation of application No. 14/415,014, filed as application No. PCT/US2013/050815 on Jul. 17, 2013, now Pat. No. 9,384,320.

(60) Provisional application No. 61/676,081, filed on Jul. 26, 2012, provisional application No. 61/673,690, filed on Jul. 19, 2012.

(56) References Cited

U.S. PATENT DOCUMENTS

| | | | |
|---|---|---|---|
| 2004/0001371 | A1 | 1/2004 | Mansuripur et al. |
| 2004/0006433 | A1 | 1/2004 | Robson et al. |
| 2004/0060987 | A1 | 4/2004 | Green |
| 2005/0053968 | A1 | 3/2005 | Bharadwaj et al. |
| 2005/0211012 | A1 | 9/2005 | Doucet |
| 2007/0012783 | A1 | 1/2007 | Mercolino |
| 2007/0012784 | A1 | 1/2007 | Mercolino |
| 2007/0113137 | A1 | 5/2007 | Ryu |
| 2009/0035777 | A1 | 2/2009 | Kokoris et al. |
| 2010/0099080 | A1 | 4/2010 | Church et al. |
| 2011/0119778 | A1 | 5/2011 | Liss |

FOREIGN PATENT DOCUMENTS

| | | |
|---|---|---|
| CN | 102083998 A | 6/2011 |
| CN | 104520864 A | 4/2015 |
| CN | 104662544 A | 5/2015 |
| IN | 101965410 A | 2/2011 |
| JP | 2003-101485 A | 4/2003 |
| JP | 2006-522356 A | 9/2006 |
| WO | 03/025123 A2 | 3/2003 |
| WO | 2003/064688 A2 | 8/2003 |
| WO | 2004/088585 A2 | 10/2004 |
| WO | 2013/178801 A2 | 12/2013 |
| WO | 2014/014991 A2 | 1/2014 |

OTHER PUBLICATIONS

Cox J P L: "Long-term data storage in DNA", Trends in Biotechnology, Elsevier Publications, Cambridge, GB, vol. 19, No. 7, Jul. 1, 2001 (Jul. 1, 2001 ), pp. 247-250, XP004246191, ISSN: 0167-7799, DOI: 10.1016/S0167-7799(01)01671-7.

G. M. Church et al: "Next-Generation Digital Information Storage in DNA". Science. vol. 337. No. 6102. Sep. 28, 2012 (Sep. 28, 2012). pp. 1628-1628. XP055082578. ISSN: 0036-8075. DOI: 10.1126jscience.1226355 the whole document.

Nick Goldman et al: "Towards practical. high-capacity. low-maintenance information storage in synthesized DNA". Nature. Jan. 1, 2013 (Jan. 1, 2013). XP055050963. ISSN: 0028-0836. DOI: 10.1038/nature11875 the whole document.

International Preliminary Report on Patentability dated Jan. 29, 2015, issued from corresponding PCT/US2013/050815.

Office Action issued for corresponding Chinese Patent Application No. 201380038507.X, dated Mar. 10, 2017.

International Search Report issued from corresponding PCT/US2016/041981, dated Nov. 30, 2016.

Church, "Next-generation digital information storage in DNA," Science, vol. 337(6102), 2012, p. 1628-1628 plus 16 pages of supplementary material for 18 pages total.

Jun. 21, 2019—(US) Notice of Allowance—U.S. Appl. No. 15/970,257.

May 29, 2020—Examination Report & Written Opinion issued for EP 13752699.2.

Arita et al., "Chapter 368: DNA Memory," Handbook of Natural Computing, pp. 1281-1318 (Jan. 1, 2012).

Tsaftaris et al., "On Designing DNA Databases for the Storage and Retrieval of Digital Signals, " Advances in Natural Computation, pp. 1192-1201 (Jul. 23, 2005).

Yamamoto et al., "Large-scale DNA memory based on the nested PCR," Natural Computing, vol. 7, No. 3, pp. 335-346 (Mar. 19, 2008).

Jul. 7, 2020—Notice of Reasons for Rejection issued for JP 2018-50193.

Oct. 10, 2020—(CN) Office Action—App. No. 201680052866.4.

Nov. 19, 2020—(EP) Supplementary European Search Report & Written Opinion—App. No. 16825066.0.

Jimenez-Sanchez, Alfonso. "A proposal for a DNA-based computer code." International Inventions Journal Biochemistry and Bioinformatics 1.1 (2013): 1-4.

Jul. 1, 2021—(CN) Office Action—App. No. 201810747946.2.

Sep. 9, 2021—(CN) Office Action—App. No. 201680052866.4.

Motea et al., "Terminal deoxynucleotidyl transferase: The story of a misguided DNA polymerase," Biochimica et Biophysica Acta, vol. 1804, pp. 1151-1166 (Jul. 29, 2009).

Feb. 1, 2022—(JP) Notice of Reasons for Rejection—App. No. 2021-001751.

Apr. 2, 2022—(CN) Decision of Rejection—App. No. 201810747946.2.

METHODS OF STORING INFORMATION USING NUCLEIC ACIDS

RELATED APPLICATION DATA

This application is a continuation application which claims priority to U.S. patent application Ser. No. 17/235,196, filed on Apr. 20, 2021; which claims priority to U.S. patent application Ser. No. 16/590,809, filed on Oct. 2, 2019; which claims priority to U.S. patent application Ser. No. 15/970,257, filed on May 3, 2018; which claims priority to U.S. patent application Ser. No. 15/175,430, filed on Jun. 7, 2016; which claims priority to U.S. patent application Ser. No. 14/415,014, filed on Jan. 15, 2015, which is a National Stage Application under 35 U.S.C. 371 of co-pending PCT application PCT/US2013/050815 designating the United States and filed Jul. 17, 2013; which claims the benefit of U.S. Provisional Application No. 61/673,690, filed on Jul. 19, 2012 and U.S. Provisional Application No. 61/676,081, filed on Jul. 26, 2012 each of which are hereby incorporated by reference in their entireties.

STATEMENT OF GOVERNMENT INTERESTS

This invention was made with government support under US Office of Naval Research N000141010144. The Government has certain rights in the invention.

SEQUENCE LISTING

The instant application contains a Sequence Listing which has been submitted electronically in XML format and is hereby incorporated by reference in its entirety. Said XML copy, created on Oct. 18, 2022, is named "Sequence_Listing_010498_01503_ST26" and is 36 KB in size.

FIELD

The present invention relates in general to methods of storing information using one or more nucleic acid sequences.

BACKGROUND

Our digital universe is growing rapidly. For example, 1.8 zettabytes ($10^{21}$) of information was created and replicated in 2011, and that amount is doubling every two years See 1. "Extracting Value from Chaos" (IDC, Framingham, MA 2011); world wide web site emc.com/collateral/analyst-reports/idc-extracting-value-from-chaos-ar.pdf. Archival data storage is often in the form of hard drives, optical media, and magnetic tapes, which offer recommended lifetimes of 5-30 years See 2. J. Rothenberg, Scientific American 272, 42-47 (1995). As digital information continues to accumulate, higher density and longer-term storage solutions are necessary. DNA has many potential advantages as a medium for information storage See 3. C. Bancroft, T. Bowler, B. Bloom, C. T. Clelland, Science 293, 1763-1765 (2001). The first instance of encoding general digital information into DNA was 35 bits in 1988 See 7. J. Davis, Art Journal 55, 70-74 (1996). Recent work deals with compression and encryption of data into DNA (usually limited to uppercase letters), and its viability in living cells See 3,8, and 9. C. Bancroft, T. Bowler, B. Bloom, C. T. Clelland, Science 293, 1763-1765 (2001)., C. Gustafsson, Nature 458, 703 (2009), and D. G. Gibson et al., Science 329, 52-56 (2010).

SUMMARY

Embodiments of the present disclosure are directed to methods of using a nucleic acid sequence or sequences including nucleotides as a medium for information storage. Common nucleotides include A, C, G, and T. Aspects of the present disclosure are directed to methods of robust, large-scale reading and writing of digital information using next generation sequencing and synthesis technologies an example of such a method is provided in schematic in FIG. 1A. According to one aspect, text and/or images is converted to megabits. According to one aspect, text and/or images converted to megabits comprise a bit stream. The megabits are then encoded into oligonucleotides. According to one aspect, the oligonucleotide includes a data block sequence. According to one aspect, the oligonucleotide includes an address sequence (such as a barcode sequence) specifying the location of the data block in the bit stream. According to one aspect, the oligonucleotide includes flanking common sequences at each end of the oligonucleotide for amplification and sequencing. According to one aspect, the oligonucleotide includes one or more or all of a data block sequence, an address sequence (such as a barcode sequence) specifying the location of the data block in the bit stream, and flanking common sequences at each end of the oligonucleotide for amplification and sequencing.

According to one aspect of the present disclosure, one bit per base is encoded. According to this aspect, a single message may be encoded in a plurality of ways, i.e., A or C for zero, G or T for the number 1. Accordingly, this aspect of the present disclosure avoids sequence features that are difficult to read or write such as extreme GC content, repeats, or secondary structure.

According to one aspect, the bit stream is divided into addressed data blocks. According to this aspect, long DNA constructs that are difficult to assemble may be avoided.

According to one aspect, many copies of each individual oligonucleotide are synthesized, stored and sequenced. Since errors in synthesis and sequencing are rarely coincident, each molecular copy corrects errors in the other copies.

According to one aspect, the process is carried out in vitro. According to this aspect, the in vitro approach avoids cloning and stability issues of in vivo approaches.

According to one aspect, high throughput, next-generation techniques are used in both DNA synthesis and sequencing to allow for encoding and decoding of large amounts of information.

According to one aspect, a method of storing information using nucleotides is provided comprising converting a format of information into a plurality of bit sequences of a bit stream with each having a corresponding bit barcode, converting the plurality of bit sequences to a plurality of corresponding oligonucleotide sequences using one bit per base encoding, synthesizing the plurality of corresponding oligonucleotide sequences, and storing the synthesized plurality of corresponding oligonucleotide sequences. According to one aspect, the oligonucleotide sequences include one or more or all of a data block sequence, an address sequence specifying the location of the data block in the bit stream, or flanking common sequences at each end of the oligonucleotide for amplification and sequencing.

According to one aspect, a method of retrieving a format of information from a plurality of synthesized oligonucleotide sequences encoding bit sequences of the format of information is provided comprising amplifying the plurality of oligonucleotide sequences, sequencing the amplified oligonucleotide sequences, converting the oligonucleotide sequences to bit sequences, and converting the bit sequences to the format of information. According to one aspect, the oligonucleotide sequences include one or more or all of a data block sequence, an address sequence specifying the location of the data block in the bit stream, or flanking common sequences at each end of the oligonucleotide for amplification and sequencing.

According to one aspect, a method of accessing a format of information from a plurality of synthesized oligonucleotide sequences encoding bit sequences of the format of information is provided comprising amplifying the plurality of oligonucleotide sequences, sequencing the amplified oligonucleotide sequences, converting the oligonucleotide sequences to bit sequences, converting the bit sequences to the format of information, and visualizing the format of information. According to one aspect, the oligonucleotide sequences include one or more or all of a data block sequence, an address sequence specifying the location of the data block in the bit stream, or flanking common sequences at each end of the oligonucleotide for amplification and sequencing.

According to one aspect, a method of storing information using nucleotides is provided comprising converting a format of information to a bit stream, encoding bit sequences into corresponding oligonucleotide sequences, synthesizing the oligonucleotide sequences, sequencing the oligonucleotide sequences, decoding the oligonucleotide sequences into bit sequences, assembling the bit sequences into a bit stream and converting the bit stream into the format of information. According to one aspect, the oligonucleotide sequences include one or more or all of a data block sequence, an address sequence specifying the location of the data block in the bit stream, or flanking common sequences at each end of the oligonucleotide for amplification and sequencing.

A method of storing information using nucleotides is provided comprising converting a first format of information to a first bit stream, encoding first bit sequences into corresponding oligonucleotide sequences, synthesizing the oligonucleotide sequences, sequencing the oligonucleotide sequences, decoding the oligonucleotide sequences into second bit sequences, assembling the second bit sequences into a second bit stream and converting the second bit stream into a second format of information. According to one aspect, the oligonucleotide sequences include one or more or all of a data block sequence, an address sequence specifying the location of the data block in the bit stream, or flanking common sequences at each end of the oligonucleotide for amplification and sequencing.

According to certain aspects, information is stored using DNA taking advantage of the DNA density. According to certain aspects, at theoretical maximum, DNA can encode 2 bits per nucleotide (nt) or 1.8 zettabytes in about 4 grams of the sodium salt See 4. Information on materials and methods is available on Science Online. According to certain aspects, a milligram of DNA is achievable with commercial oligo sizes and sequencing technologies known to those of skill in the art (48 bit barcode+128 bit payload), and for 100× coverage, a petabyte ($10^{15}$) is achievable. This amount could be stored in a 1536 well plate to provide an exabyte, with a thousand of those (0.5 m a side cube) making a zettabyte ($8×10^{21}$ bits). Subsets of the stored data can be stored in a mixture and retrieved separately by using orthogonal (i.e. minimally cross-priming) flanking primers. See Church GM, Kieffer-Higgins S (1988) Multiplex Sequencing; and Kosuri S, Eroshenko N, LeProust E, Super M, Way J, Li JB, Church GM (2010) A Scalable Gene Synthesis Platform Using High-Fidelity DNA Microchips. Nature Biotech. 28(12):1295-9.

According to certain aspects, DNA does not require a planar surface for storage, is easily preserved, and has been recovered after millennia See 5 and 6. 5. J. Bonnet et al., Nucleic Acids Research 38, 1531-1546 (2010) and 6.S. Pääbo et al., M. A. Uyterlinde et al., Eds. Annual Review of Genetics 38, 645-679 (2004). According to certain aspects, DNA's essential biological role provides access to natural reading and writing enzymes and ensures that DNA will remain a readable standard for the foreseeable future.

BRIEF DESCRIPTION OF THE DRAWINGS

The patent or application file contains at least one drawing executed in color. Copies of this patent or patent application publication with color drawing(s) will be provided by the Office upon request and paymeny of the necessary fee. The foregoing and other features and advantages of the present invention will be more fully understood from the following detailed description of illustrative embodiments taken in conjunction with the accompanying drawing in which.

DETAILED DESCRIPTION

Figure 1A:
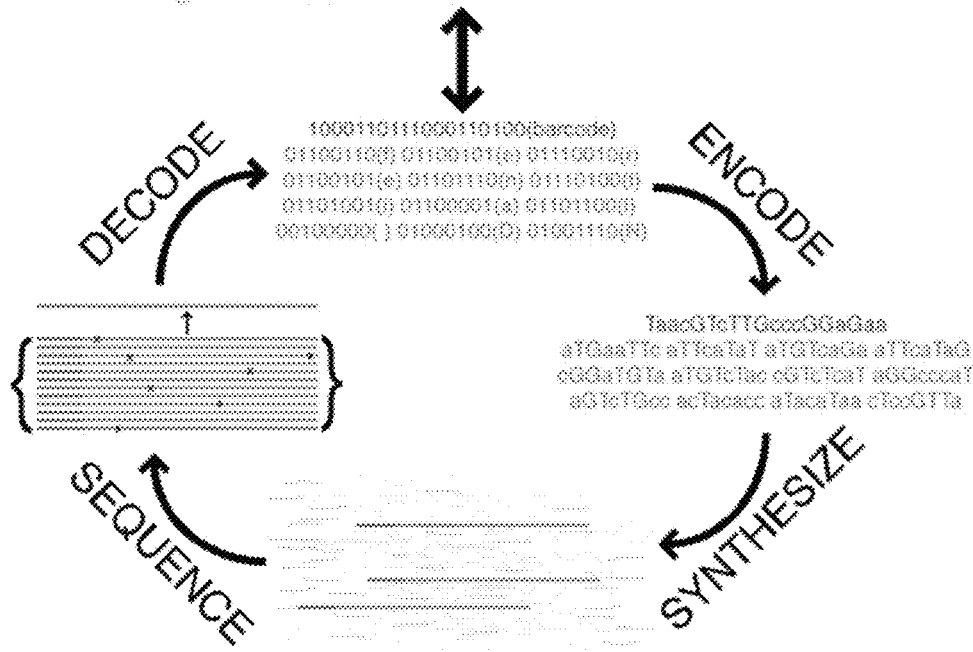
FIG. 1A is a schematic of DNA information storage. A 12-byte portion of a sentence within the encoded html book is converted to bits (blue) with a 19-bit barcode (red) that determines the location of the encoded bits within the overall book. The bit sequence is then encoded to DNA using a 1 bit per base encoding (ac=0; TG=1), while also avoiding 4 or more nucleotide repeats and balancing GC content. The entire 5.27 megabit html book used 54,898 oligonucleotides and was synthesized and eluted from a DNA microchip. After amplification (common primer sequences to all oligonucleotides are not shown), the oligonucleotide library was sequenced using next-generation sequencing. Individual reads with the correct barcode and length were screened for consensus, and then reconverted to bits obtaining the original book. In total, the writing, amplification, and reading resulted in 10 bit errors out of 5.27 megabits.

The present invention is directed to methods of storing information using oligomers. Such oligomers can be formed from monomers. Exemplary monomers include nucleotides. Exemplary oligomers include oligonucleotides. According to one aspect, a method of encoding information is provided where a sequence of bits are converted to a sequence of nucleotides, where the sequence of nucleotides is an oligonucleotide. According to one aspect, commercially available methods of nucleic acid synthesis are used. According to one aspect, commercially available methods of nucleic acid amplification are used. According to one aspect, commercially available methods of nucleic acid sequencing are used.

According to one aspect, a portion or portions of a format of information, such as an html format of information, such as an html book with text and/or images, is converted to bits, i.e. zeros and ones, and a bit barcode is added to form a bit sequence, i.e. a series of zeros and ones as commonly understood. Other formats of information that can be converted to bits are known to those of skill in the art. According to one aspect, the portion of an html format of information to be converted into bits may be referred to as a byte portion. The bit barcode can determine the location of the encoded bits within the overall html format of information. The bit sequence is then converted (encoded) to a sequence of nucleotides, i.e., an oligonucleotide or DNA using a 1 bit per base encoding (ac=0; TG=1) to form a corresponding encoded oligonucleotide sequence, i.e. the oligonucleotide sequence corresponds to or encodes for the bit sequence. According to one aspect, 4 or more nucleotide repeats are avoided and GC content is balanced. A plurality of bit sequences are created corresponding to a portion of or the entire html format of information. Accordingly, a plurality of corresponding encoded oligonucleotide sequences are created which together may be referred to as a library. The library of encoded oligonucleotide sequences represents the html format of information. The encoded oligonucleotide sequences are then synthesized using methods known to those of skill in the art, such as using a DNA microchip. The synthesized oligonucleotides are then amplified using methods known to those of skill in the art to form a library of oligonucleotides. The library of oligonucleotides is then sequenced using methods known to those of skill in the art, such as next-generation sequencing methods. The sequenced oligonucleotides are then converted into bit sequences corresponding to the html format of information. The bit sequences can be converted to the format of information using methods known to those of skill in the art. The format of information can be visualized or displayed using methods and devices known to those of skill in the art.

Terms and symbols of nucleic acid chemistry, biochemistry, genetics, and molecular biology used herein follow those of standard treatises and texts in the field, e.g., Komberg and Baker, *DNA Replication,* Second Edition (W. H. Freeman, New York, 1992); Lehninger, *Biochemistry,* Second Edition (Worth Publishers, New York, 1975); Strachan and Read, *Human Molecular Genetics,* Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

As used herein, the term "bit" is to be understood according to its common meaning to one of skill in the art. The term "bit" may be a contraction of "binary digit" and may refer to a basic capacity of information in computing and telecommunications. A "bit" represents either 1 or 0 (one or zero) only. The representation may be implemented, in a variety of systems, by means of a two state device.

As used herein, the terms "nucleic acid molecule," "nucleic acid sequence," "nucleic acid fragment" and "oligomer" are used interchangeably and are intended to include, but are not limited to, a polymeric form of nucleotides that may have various lengths, including either deoxyribonucleotides or ribonucleotides, or analogs thereof. Oligomers for use in the present invention can be fully designed, partially designed (i.e., partially randomized) or fully randomized. In certain aspects of the invention, a pool of nucleic acids contains single-stranded 90-mers of DNA.

In general, "amplifying" includes the production of copies of a nucleic acid molecule via repeated rounds of primed enzymatic synthesis. "In situ" amplification indicated that the amplification takes place with the template nucleic acid molecule positioned on a support or a bead, rather than in solution. In situ amplification methods are described in U.S. Pat. No. 6,432,360.

Varied choices of polymerases exist with different properties, such as temperature, strand displacement, and proofreading. Amplification can be isothermal, as described above and in similar adaptation such as multiple displacement amplification (MDA) described by Dean et al., Comprehensive human genome amplification using multiple displacement amplification, *Proc. Natl. Acad. Sci. U.S.A.,* vol. 99, p. 5261-5266. 2002; also Dean et al., Rapid amplification of plasmid and phage DNA using phi29 DNA polymerase and multiply-primed rolling circle amplification, *Genome Res.,* vol. 11, p. 1095-1099. 2001; also Aviel-Ronen et al., Large fragment Bst DNA polymerase for whole genome amplification of DNA formalin-fixed paraffin-embedded tissues, *BMC Genomics,* vol. 7, p. 312. 2006. Amplification can also cycle through different temperature regiments, such as the traditional polymerase chain reaction (PCR) popularized by Mullis et al., Specific enzymatic amplification of DNA in vitro: The polymerase chain reaction. *Cold Spring Harbor Symp. Quant. Biol.,* vole 51, p. 263-273. 1986. Variations more applicable to genome amplification are described by Zhang et al., Whole genome amplification from a single cell: implications for genetic analysis, *Proc. Natl. Acad. Sci. U.S.A.,* vol. 89, p. 5847-5851. 1992; and Telenius et al., Degenerate oligonucleotide-primed PCR: general amplification of target DNA by a single degenerate primer, *Genomics,* vol. 13, p. 718-725. 1992. Other methods include Polony PCR described by Mitra and Church, In situ localized amplification and contact replication of many individual DNA molecules, *Nuc. Acid. Res.,* vole 27, pages e34. 1999; emulsion PCR (ePCR) described by Shendure et al., Accurate multiplex polony sequencing of an evolved bacterial genome, *Science,* vol. 309, p. 1728-32. 2005; and Williams et al., Amplification of complex gene libraries by emulsion PCR, *Nat. Methods,* vol. 3, p. 545-550. 2006. Any amplification method can be combined with a reverse transcription step, a priori, to allow amplification of RNA. According to certain aspects, amplification is not absolutely required since probes, reporters and detection systems with sufficient sensitivity can be used to allow detection of a single molecule using template non-hybridizing nucleic acid structures described. Ways to adapt sensitivity in a system include choices of excitation sources (e.g. illumination) and detection (e.g. photodetector, photomultipliers). Ways to adapt signal level include probes allowing stacking of reporters, and high intensity reporters (e.g. quantum dots) can also be used.

Amplification methods useful in the present disclosure may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:

7790), the amplification methods described in U.S. Pat. Nos. 6,391,544, 6,365,375, 6,294,323, 6,261,797, 6,124,090 and 5,612,199, or any other nucleic acid amplification method using techniques well known to those of skill in the art. In exemplary embodiments, the methods disclosed herein utilize PCR amplification.

In certain exemplary embodiments, methods for amplifying nucleic acid sequences are provided. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683, 195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277: 7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, *PCR: A Practical Approach* and *PCR2: A Practical Approach* (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 68-78° C.

The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 µL. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research*, 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) *Anal. Biochem.*, 273:221-228 (two-color real-time PCR). Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., *Biotechniques*, 26:112-126 (1999); Becker-Andre et al., *Nucleic Acids Research*, 17:9437-9447 (1989); Zimmerman et al., *Biotechniques*, 21:268-279 (1996); Diviacco et al., *Gene*, 122:3013-3020 (1992); Becker-Andre et al., *Nucleic Acids Research*, 17:9437-9446 (1989); and the like.

Sequencing methods useful in the present disclosure include Shendure et al., Accurate multiplex polony sequencing of an evolved bacterial genome, *Science*, vol. 309, p. 1728-32. 2005; Drmanac et al., Human genome sequencing using unchained base reads on self-assembling DNA nanoarrays, *Science*, vol. 327, p. 78-81. 2009; McKernan et al., Sequence and structural variation in a human genome uncovered by short-read, massively parallel ligation sequencing using two-base encoding, *Genome Res.*, vol. 19, p. 1527-41. 2009; Rodrigue et al., Unlocking short read sequencing for metagenomics, *PLoS One*, vol. 28, e11840. 2010; Rothberg et al., An integrated semiconductor device enabling non-optical genome sequencing, *Nature*, vol. 475, p. 348-352. 2011; Margulies et al., Genome sequencing in microfabricated high-density picolitre reactors, *Nature*, vol. 437, p. 376-380. 2005; Rasko et al. Origins of the *E. coli* strain causing an outbreak of hemolytic-uremic syndrome in Germany, *N. Engl. J. Med.*, Epub. 2011; Hutter et al., Labeled nucleoside triphosphates with reversibly terminating aminoalkoxyl groups, *Nucleos. Nucleot. Nucl.*, vol. 92, p. 879-895. 2010; Seo et al., Four-color DNA sequencing by synthesis on a chip using photocleavable fluorescent nucleotides, *Proc. Natl. Acad. Sci. USA.*, Vol. 102, P. 5926-5931 (2005); Olejnik et al.; Photocleavable biotin derivatives: a versatile approach for the isolation of biomolecules, *Proc. Natl. Acad. Sci. U.S.A.*, vol. 92, p. 7590-7594. 1995; U.S. Pat. No. 5,750,34; US 2009/0062129 and US 2009/0191553.

In general, the terms "nucleic acid molecule," "nucleic acid sequence," "nucleic acid fragment," "oligonucleotide" and "polynucleotide" are used interchangeably and are intended to include, but not limited to, a polymeric form of nucleotides that may have various lengths, either deoxyribonucleotides (DNA) or ribonucleotides (RNA), or analogs thereof. A oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may optionally include one or more non-standard nucleotide(s), nucleotide analog(s) and/or modified nucleotides.

Embodiments of the present disclosure include naturally occurring or synthetic oligomers known to those of skill in the art. Such oligomers include oligonucleotides or polynucleotides (such as DNA or RNA), polypeptides (like collagen and vancomycin), polyketides (like fats and tetracycline), polysaccharides (like cellulose and starch), polyterpenes (like cholesterol and rubber), polyamino-acids (like lignin and polyalkaloids), polypyrroles (like heme and vitamin B12), and polyesters (like PHA, PHV). Oligomers include those having bio-inspired classes of bonds. See table 1 of US2008/0096253. Additional oligomers include non-biological polymers, such as linear polymers including polysiloxanes, polyacrylamides, and the like. Such oligomers may have sufficient thermal stability or ease of detection in nanopores or other polymer sequencing devices.

Examples of modified nucleotides include, but are not limited to diaminopurine, $S^2T$, 5-fluorouracil, 5-bromouracil, 5-chlorouracil, 5-iodouracil, hypoxanthine, xantine, 4-acetylc yto sine, 5-(c arbo xyhydroxylmethyl)uracil, 5-c arboxymethylaminomethyl-2-thiouridine, 5-c arboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxyc arboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A (2012) KlenTaq polymerase replicates unnatural base pairs by inducing a Watson-Crick geometry, Nature Chem. Biol. 8:612-614; Seo Y J, Malyshev D A, Lavergne T, Ordoukhanian P, Romesberg F E. J Am Chem Soc. 2011 Dec. 14;133(49):19878-88, Site-specific labeling of DNA and RNA using an efficiently replicated and transcribed class of unnatural base pairs; Switzer CY, Moroney SE, Benner SA. (1993) Biochemistry. 32(39):10489-96. Enzymatic recognition of the base pair between isocytidine and isoguanosine; Yamashige R, Kimoto M, Takezawa Y, Sato A, Mitsui T, Yokoyama S, Hirao I. Nucleic Acids Res. 2012 Mar.;40(6): 2793-806. Highly specific unnatural base pair systems as a third base pair for PCR amplification; and Yang Z, Chen F, Alvarado JB, Benner SA. J Am Chem Soc. 2011 Sep. 28;133(38):15105-12, Amplification, mutation, and sequencing of a six-letter synthetic genetic system.

The 6 pairs below (A-T, G-C, Z-P, Ds-Px, NAM-SSICS, isoC-isoG) have been shown to be compatible with polymerases and orthogonal to each other (i.e. low levels of cross-pairing).

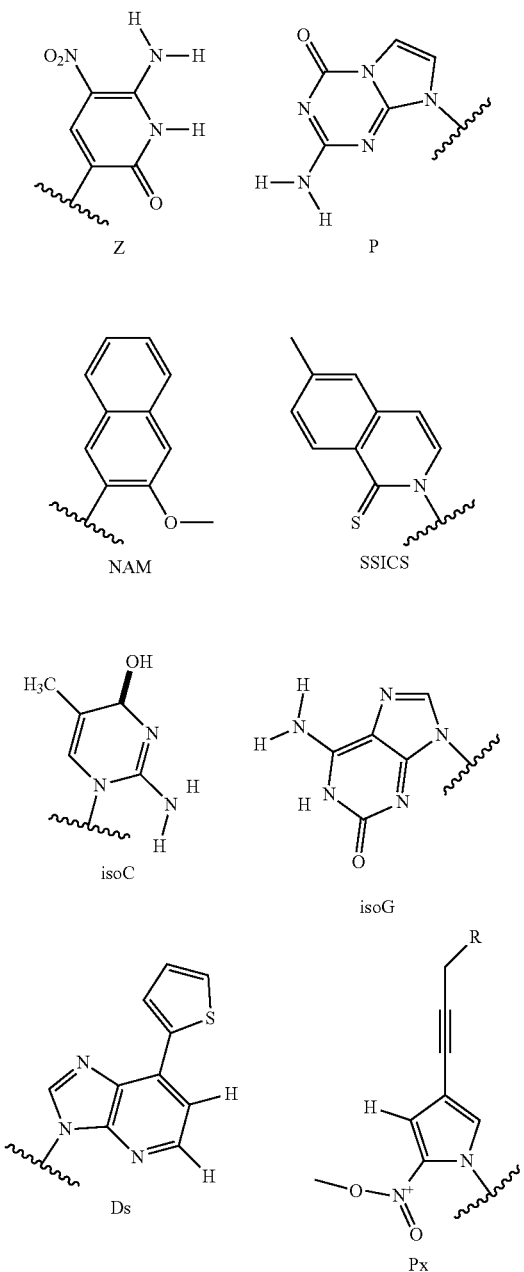

-continued

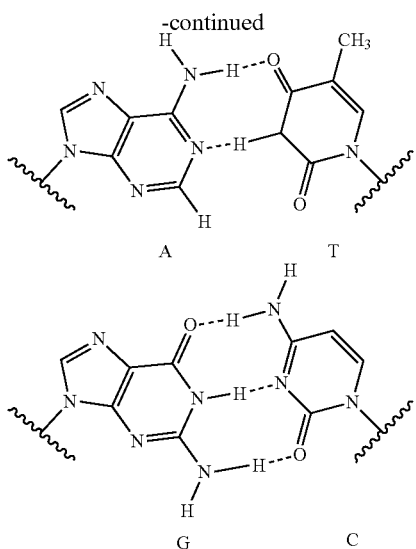

In certain exemplary embodiments, oligonucleotide sequences may be prepared using one or more of the phosphoramidite linkers and/or sequencing by ligation methods known to those of skill in the art. Oligonucleotide sequences may also be prepared by any suitable method, e.g., standard phosphoramidite methods such as those described herein below as well as those described by Beaucage and Carruthers ((1981) *Tetrahedron Lett.* 22: 1859) or the triester method according to Matteucci et al. (1981) *J. Am. Chem. Soc.* 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain exemplary embodiments, oligonucleotide sequences may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) *Proc. Natl. Acad. Sci. U.S.A.* 93:13555; Synthetic DNA Arrays In Genetic Engineering, Vol. 20:111, Plenum Press (1998); Duggan et al. (1999) *Nat. Genet.* S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597.

In certain exemplary embodiments, one or more oligonucleotide sequences described herein are immobilized on a support (e.g., a solid and/or semi-solid support). In certain aspects, an oligonucleotide sequence can be attached to a support using one or more of the phosphoramidite linkers described herein. Suitable supports include, but are not limited to, slides, beads, chips, particles, strands, gels, sheets, tubing, spheres, containers, capillaries, pads, slices, films, plates and the like. In various embodiments, a solid support may be biological, nonbiological, organic, inorganic, or any combination thereof. When using a support that is substantially planar, the support may be physically separated into regions, for example, with trenches, grooves, wells, or chemical barriers (e.g., hydrophobic coatings, etc.). In certain exemplary embodiments, a support is a microarray. As used herein, the term "microarray" refers in one embodiment to a type of assay that comprises a solid phase support having a substantially planar surface on which there is an array of spatially defined non-overlapping regions or sites that each contain an immobilized hybridization probe. "Substantially planar" means that features or objects of interest, such as probe sites, on a surface may occupy a volume that extends above or below a surface and whose dimensions are small relative to the dimensions of the surface. For example, beads disposed on the face of a fiber optic bundle create a substantially planar surface of probe sites, or oligonucleotides disposed or synthesized on a porous planar substrate creates a substantially planar surface. Spatially defined sites may additionally be "addressable" in that its location and the identity of the immobilized probe at that location are known or determinable.

Oligonucleotides immobilized on microarrays include nucleic acids that are generated in or from an assay reaction. Typically, the oligonucleotides or polynucleotides on microarrays are single stranded and are covalently attached to the solid phase support, usually by a 5'-end or a 3'-end. In certain exemplary embodiments, probes are immobilized via one or more of the cleavable linkers described herein. The density of non-overlapping regions containing nucleic acids in a microarray is typically greater than 100 per cm², and more typically, greater than 1000 per cm². Microarray technology relating to nucleic acid probes is reviewed in the following exemplary references: Schena, Editor, *Microarrays: A Practical Approach* (IRL Press, Oxford, 2000); Southern, *Current Opin. Chem. Biol.*, 2: 404-410 (1998); *Nature Genetics* Supplement, 21:1-60 (1999); and Fodor et al, U.S. Pat. Nos. 5,424,186; 5,445,934; and 5,744,305.

Methods of immobilizing oligonucleotides to a support are known in the art (beads: Dressman et al. (2003) *Proc. Natl. Acad. Sci. USA* 100:8817, Brenner et al. (2000) *Nat. Biotech.* 18:630, Albretsen et al. (1990) *Anal. Biochem.* 189:40, and Lang et al. *Nucleic Acids Res.* (1988) 16:10861; nitrocellulose: Ranki et al. (1983) *Gene* 21:77; cellulose: Goldkorn (1986) *Nucleic Acids Res.* 14:9171; polystyrene: Ruth et al. (1987) Conference of Therapeutic and Diagnostic Applications of Synthetic Nucleic Acids, Cambridge U.K.; teflon-acrylamide: Duncan et al. (1988) *Anal. Biochem.* 169:104; polypropylene: Polsky-Cynkin et al. (1985) *Clin. Chem.* 31:1438; nylon: Van Ness et al. (1991) *Nucleic Acids Res.* 19:3345; agarose: Polsky-Cynkin et al., *Clin. Chem.* (1985) 31:1438; and sephacryl: Langdale et al. (1985) *Gene* 36:201; latex: Wolf et al. (1987) *Nucleic Acids Res.* 15:2911).

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell,* 3d edition, Garland Publishing, 1994.

Sequencing primers according to the present disclosure are those that are capable of binding to a known binding region of the target polynucleotide and facilitating ligation of an oligonucleotide probe of the present disclosure. Sequencing primers may be designed with the aid of a computer program such as, for example, DNAWorks, or Gene2Oligo. The binding region can vary in length but it should be long enough to hybridize the sequencing primer. Target polynucleotides may have multiple different binding regions thereby allowing different sections of the target polynucleotide to be sequenced. Sequencing primers are selected to form highly stable duplexes so that they remain hybridized during successive cycles of ligation. Sequencing primers can be selected such that ligation can proceed in either the 5' to 3' direction or the 3' to 5' direction or both. Sequencing primers may contain modified nucleotides or bonds to enhance their hybridization efficiency, or improve their stability, or prevent extension from a one terminus or the other.

According to one aspect, single stranded DNA templates (ssDNA) are prepared by RCA as described above to be used with sequencing primers. Alternatively single stranded template is attached to beads or nanoparticles in an emulsion and amplified through ePCR. The result is clonal beads with a single amplified ssDNA template.

For the purpose of identifying several template nucleotide sequences in parallel, the templates are diluted in PBS buffer pH 7.4, and either bound to a patterned or non-patterned substrate utilizing various attachment methods, such as Biotin-Strepavidin, azide-alkyle (e.g. click chemistry), NHS-ester or Silanization (e.g. aldehyde-, epoxy-, aminosilane). According to one aspect, rolonies are attached to a patterned surface, such as a $SiO_2$ solid surface, treated with 1% aminosilane (v/v) and let to interact for a period of time (typically between 5 minutes to 2 hours). Any unbound templates are then washed away using Wash 1 buffer.

Next, a sequencing primer is prepared and hybridized to the sequencing primer hybridizing site. According to certain aspects, sequencing primers can be prepared which can hybridize to a known sequence of the template. Alternatively, during template preparation, adapters with a known nucleic acid sequence are added to the unknown nucleic acid sequence by way of ligation, amplification, transposition or recombination according to methods known to those of skill in the art and described herein. Still alternatively, sequencing primers having a certain level of degeneracy could be used to hybridize to certain positions along the template. According to one aspect, primer degeneracy is used to allow primers to hybridize semi-randomly along the template. Primer degeneracy is selected based on statistical methods known to those of skill in the art to facilitate primers hybridizing at certain intervals along the length of the template. According to this aspect, primers can be designed having a certain degeneracy which facilitates binding every N bases, such as every 100 bases, every 200 bases, every 2000 bases, every 100,000 bases. The binding of the primers along the length of the template is based on the design of the primers and the statistical likelihood that a primer design will bind about every N bases along the length of the template. Since the sequencing primer P1 will be extended by ligation, the terminal group of the sequencing primer is typically synthesized to be ready to be covalently joined to the oligonucleotide probe by the DNA ligase. If the ligation occurs between the 5'end of the sequencing primer and the 3'end of the oligonucleotide probe, a phosphate group (5'-$PO_4$) must be present on the sequencing primer while a hydroxyl group (3'-OH) on the oligonucleotide probe, and vice-versa. To hybridize the sequencing primer to the sequencing primer hybridizing site, 1 uM of the sequencing primer diluted in 5X SSPE buffer is used. The mixture is then incubated for a few minutes above room temperature to encourage proper annealing (typically between 1 to 5 minutes, at temperature between 25 and 55° C.).

According to certain aspects, oligonucleotide sequences may be prepared using ink jet techniques known to those of skill in the art, electrochemical techniques known to those of skill in the art, microfluidic techniques known to those of skill in the art, photogenerated acids known to those of skill in the art, or photodeprotected monomers known to those of skill in the art. Such techniques have the advantage of making oligonucleotides at high speed, low cost, fewer toxic chemicals, enhanced portability and ability to interleave DNA biochemistry (e.g. modifications, polymerases, hybridization etc.) with de novo (digital or analog) synthesis. For example, spatially patterned light, either directly from camera optics or from Digital Micromirror Display devices (DMD), can be used with aqueous chemistry. See US2003/0228611. For example, a template-independent polymerase like Terminal deoxynucleotidyl Transferase (TdT) or poly (A) polymerase—alternatively, a template-dependent polymerase like Taq or Phi29 derivatives, can have their basic polymerase function, base-specificity or fidelity programmable by light by incorporating an azobenzene amino acid (see Hoppmann C, Schmieder P, Heinrich N, Beyermann M. (2011) Chembiochem.12(17):2555-9. doi: 10.1002/cbic.201100578. Epub 2011 Oct. 13, Photoswitchable click amino acids: light control of conformation and bioactivity) into the active site of the polymerase or 5'→3' exonuclease domains (if present).

Light sensitive neurons (optogenetics) can trigger ion-sensitive polymerases (see Zamft B, Marblestone A, Kording K, Schmidt D, Martin-Alarcon D, Tyo K, Boyden E, Church GM(2012) Measuring Cation Dependent DNA Polymerase Fidelity Landscapes by Deep Sequencing. PLoS One, in press) or, for some applications, the ion flux patterns themselves can constitute the stored datasets.

The de novo polymers can be stored and read with or without polymerase amplification. Amplification can be via thermal cycling or isothermal. The amplicons can be short (100 to 200 mers as is convenient for current chemical synthesis or up to 1 Mbp as might be achievable with polymerases.

The nucleotide type incorporated can be determined by: a) the intersection of a light pulse coincident with a particular dNTP (or rNTP or other monomer class) present at that time point in a cyclic pattern of dNTP solutions. b) 'caged' (i.e. photo-activatable or photo-inactivatable) dNTPs, rNTPs or cations. c) base-specific, light-modulated steric or conformational selectivity (see Hoppmann C, Schmieder P, Heinrich N, Beyermann M. (2011) Chembiochem.12(17):2555-9. doi: 10.1002/cbic.201100578. Epub 2011 Oct. 13. Photoswitchable click amino acids: light control of conformation and bioactivity). Poly(A) polymerase is particularly useful since its specificity for ATp relative to other rNTPs is due to a conformational change which can be mimicked by a photo-sensitive amino acid linkage (like azobenzene, with or without crosslinking).

This invention is further illustrated by the following example, which should not be construed as limiting. The contents of all references, patents and published patent applications cited throughout this application are hereby incorporated by reference in their entirety for all purposes.

EXAMPLE I

Written Information to be Stored Using DNA

An HTML version of a draft book called *Regenesis* (Church G M and Regis E) to be published by Basic Books (New York, NY) was selected to demonstrate modern formatting, images, and javascript. As with typical web pages, Universal Character Set Transformation Format, 8-bit (UTF-8), a variable-width encoding, which is backwards compatible with ASCII and UNICODE for special characters and fonts were used. There were 11 images that are black-and-white and JPEG encoded (typically a 10:1 data compression with little loss in quality). These were embedded "inline" (i.e. not separate files) in the html in base64 format. A consensus bit error in the middle of any of these JPEG segments would only affect data downstream within that segment. A bit error in the text will affect at most the 12 characters in that oligonucleotide containing the error. The javascript is a simple display of a 37-byte text string (mnemonic encoding of the genetic code) that can curve dynamically to follow the cursor position. According to the present disclosure, DNA (like other digital media) can encode executable directives for digital machines.

EXAMPLE II

Encoding the Written Information into DNA

The book was converted to html format (with embedded jpg images). The book was read in bit form and then individual bits were converted to A or C for 0 and T or G for 1. Bases were chosen randomly while disallowing homopolymer runs greater than three. Addresses of the bitstream were 19 bits long and numbered consecutively, starting from 0000000000000000001. The script Bits2DNA.pl (see code section) is the program used for encoding the html file into DNA segments.

EXAMPLE III

Synthesis and Amplification 54,898 oligonucleotides were synthesized on an Agilent Oligo Library Synthesis microarray platform. DNA was eluted by Agilent to give an ~10 picomole pool of oligonucleotides in 100 μL TE (10 mM Tris-Cl pH 7.5, 0.1 mM EDTA).

The libraries were amplified as follows. 1μL (~10 femtomole expected) of library was used in a 50 μL PCR amplification reaction using 200 nM each of primers MD-Test-1F and MD-Test-1R for 6 cycles using Sybr Fast Master Mix (Kapa Biosystems) in a BioRad CFX96 Real-Time PCR machine and monitored the Sybr Green channel during amplification.

95° C. for 3 min
95° C. for 10 sec
60° C. for 30 sec
Read Sybr Green Channel
Goto Step 2 for a total of 10 cycles
68° C. for 30 sec
Hold at 4° C.

The resulting PCR product was purified using Qiagen MinElute PCR cleanup column according to manufacturer's instructions into 10 μL of Buffer EB (10 mM Tris-Cl, pH 8.5). The eluted DNA gave a concentration of 36.8 ng/μL (A260/A280=1.85) as measured by a NanoDrop 2000 c spectrophotometer.

Two tubes of 1 μL of 1:11 diluted (in water) amplification reaction were amplified for nine cycles using the same conditions but this time using 200 nM of PE-PCR Primer 1.0-F and PE-PCR Primer 2.0-R. PCR reactions were cleaned up using Ampure beads per manufacturer's suggestion (Agencourt) to remove residual primers and resuspended in 50 μL of TE. The final product was ~22 ng/μL as quantified both through NanoDrop and agarose gel imaging. Primers used are as follows with * denoting phosphorothioate linkage.

```
>MD Test 1-F
                                              (SEQ ID NO: 1)
ACACTCTTTCCCTACACGACGCTCTTCCGATC*T >MD Test 1-R
                                              (SEQ ID NO: 2)
CTCGGCATTCCTGCTGAACCGCTCTTCCGATC*T >PE PCR Primer 1.0-F
                                              (SEQ ID NO: 3)
AATGATACGGCGACCACCGAGATCTACACTCTTTCCCTACACGACGCTC

TTCCGATC*T

>PE PCR Primer 2.0-R
                                              (SEQ ID NO: 4)
CAAGCAGAAGACGGCATACGAGATCGGTCTCGGCATTCCTGCTGAACCG

CTCTTCCGATC*T
```

EXAMPLE IV

Sequencing and Processing

The amplified library was sequenced by loading 1 mL of 14 pM library (14 fmoles; 1:1000 of the amplified library) on a single lane of a HiSeq 2000 using paired end 100 reads. From the lane we got 346,151,426 million paired reads with 87.14% >=Q30 and mean Q score of 34.16. Since a 115 bp construct with paired 100 bp reads was being sequenced, SeqPrep See 11 J. St. John, SeqPrep https://github.com/jstjohn/SeqPrep (2011) was used to combine overlapping reads into a single contig using the following command (for a single tile of the HiSeq lane): SeqPrep-f MTMC2_NoIndex_L006_R1_002.fastq.gz -r MTMC2 NoIndex L006 R2 002.fastq.gz-1 tile2rl.fastq.gz-2 tile2r2.fastq.gz-s tile2-merged.fastq.gz-E tile2-align.txt.gz-o 50-m 0.1-n 0.8.

After SeqPrep, 292,371,030 contigs were formed. The contigs were aligned to the reference using Bowtie2 version 2.0.0-beta5 See 17 B. Langmead, S. L. Salzberg, Nature Methods 9, 357-360 (2012) and SamTools version 0.1.18 See 18 H. Li et al., Bioinformatics 25, 2078-2079 (2009) using the following command: zcat *merged*|bowtie2-p 10-end-to-end-x . . . / . . . / . . . /agilentlib-U-|samtools view-bS->alltiles-merged.bam.

After alignment, 267,993,389 (92%) aligned to one member of the synthetic library giving average coverage of 4882±1261 (±1 standard deviation). SeqPrepped contigs that give the full-length 115 bp contig were filtered, resulting in 190,284,472 reads and 3419±998 average coverage. On average for each member of the library, ~69.5% ±0.4 of the reads were of full length. The construct with the fewest number of reads was an oligo md-37545, which had 94 and 9 reads before and after 115 bp filtering; the resulting consensus was still correct for this oligo.

Figure 2:
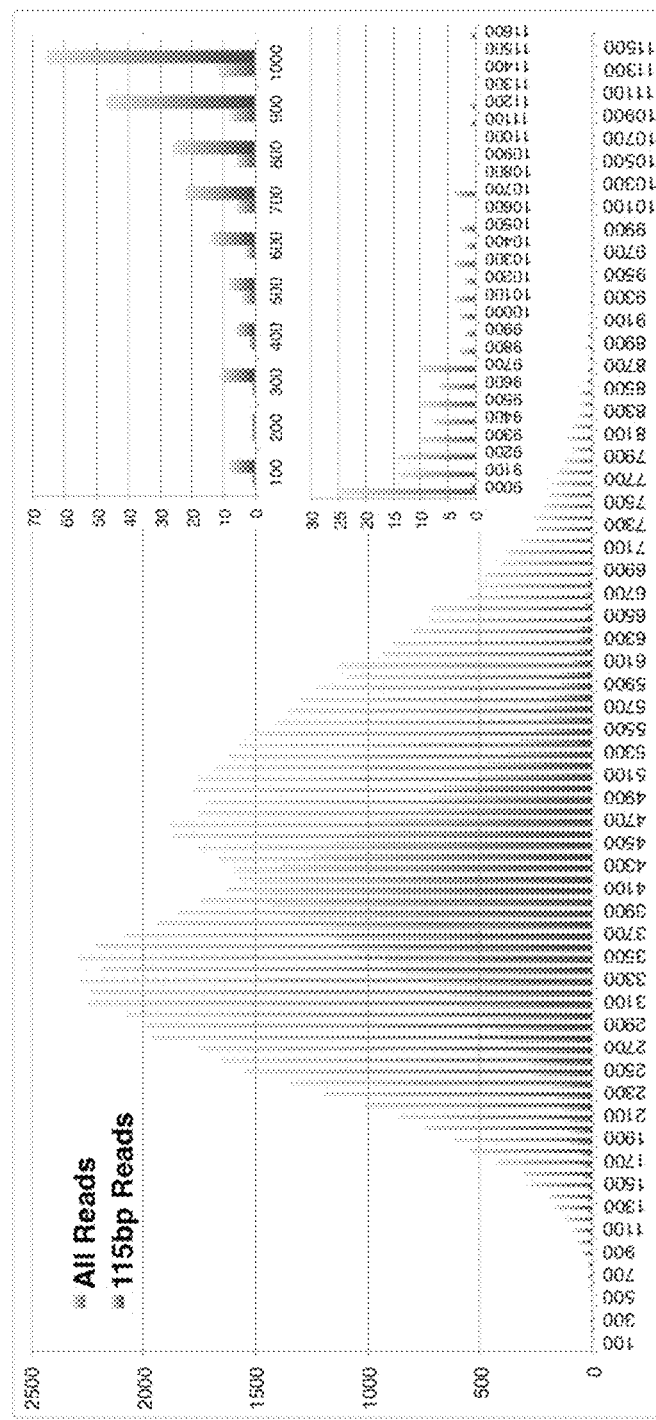
FIG. 2 is a histogram of the number of observations for each member of the designed library

FIG. 2 is a histogram of the number of observations for each member of the designed library. All reads that formed contigs from SeqPrep (i.e., had overlaps between reads) were aligned against the synthesized library using Bowtie2, binned and plotted (red). The same information is displayed in green for only contigs 115 bp in length. Insets show zoomed in views of the distribution tails.

EXAMPLE V

Errors

From the consensus library, discrepancies were found between designed and read sequences that are summarized in Table 1 below. As shown, 22 discrepancies were found, 10 of which resulted in bit errors (bolded). Most of the errors (20/22) were located within the last 15 bases of the sequence where there was only single coverage during sequencing. In addition, most of the errors (18/22) resulted in runs of at least 3 consecutive repeated nucleotides. Screening out homopolymer reads of 4 or more repeated nucleotides (greyed boxes) would result in 12 discrepancies, 7 of which are bit errors.

TABLE 1

| Barcode | Error Position | Error Type | Bit Error | Reference Context | Read Context | Homo-polymer |
|---|---|---|---|---|---|---|
| AACTGTCGCTATTC ACTCA (SEQ ID NO: 5) | 115 | A->G | yes | CAC-A- | CAC-G- | no |
| ACTAACGCACCTG GAATCA (SEQ ID NO: 6) | 106 | A->C | no | CTT-A-CCT | CTT-C-CCT | no |
| ACTTTCGGCATGAG TACCC (SEQ ID NO: 7) | 103 | A->C | no | CGC-A-CCC | CGC-C-CCC | yes |
| AGCGGCTCGTCGGT GTCCC (SEQ ID NO: 8) | 40 | T->C | yes | GGT-T-CCG | GGT-C-CCG | no |
| ATACGGCTCATTAC AAACC (SEQ ID NO: 9) | 105 | G->C | yes | TCT-G-CCC | TCT-C-CCC | yes |
| ATGCGGGCAAATC ACAGCA (SEQ ID NO: 10) | 106 | A->C | no | AAC-A-CCT | AAC-C-CCT | yes |
| ATGGCCGTAATGG AGAAAC (SEQ ID NO: 11) | 102 | C->A | no | TAG-C-AAG | TAG-A-AAG | no |
| ATGTTCTGAATTAG CGCCC (SEQ ID NO: 12) | 108 | C->G | yes | CAA-C-GAG | CAA-G-GAG | no |
| CAATGTAGATCCTC GAAAC (SEQ ID NO: 13) | 106 | A->C | no | CAG-A-CCC | CAG-C-CCC | yes |
| CCGGCCTAAACGG CACGCC (SEQ ID NO: 14) | 106 | A->C | no | CTC-A-CCT | CTC-C-CCT | yes |
| CGATATTCGGGAA CACCCA (SEQ ID NO: 15) | 102 | G->C | yes | AAC-G-CCC | AAC-C-CCC | yes |
| CGATATTCGGGAA CACCCA (SEQ ID NO: 16) | 106 | A->C | no | CCC-A-CCT | CCC-C-CCT | yes |
| CGGCGGAGCGGAG ACGCCA (SEQ ID NO: 17) | 106 | C->A | no | AGG-C-AAG | AGG-A-AAG | no |
| CTGCTCTTCAACCG CTACA (SEQ ID NO: 18) | 115 | T->G | no | CGA-T- | CGA-G- | no |

TABLE 1-continued

| Barcode | Error Position | Error Type | Bit Error | Reference Context | Read Context | Homo-polymer |
|---|---|---|---|---|---|---|
| GGTAATTTCTAGTACAGCC (SEQ ID NO: 19) | 105 | A->C | no | GCA-A-CCC | GCA-C-CCC | yes |
| GGTCGCATAAACTTGACCC (SEQ ID NO: 20) | 105 | A->G | yes | CGC-A-CGA | CGC-G-GGA | no |
| GGTCGCATAAACTTGACCC (SEQ ID NO: 21) | 106 | C->G | yes | GCA-C-GAG | GCG-G-GAG | no |
| GTGCCAATAAAGTGGTCCC (SEQ ID NO: 22) | 102 | T->C | yes | TCG-T-CCG | TCG-C-CCG | no |
| GTGCCAATAAAGTGGTCCC (SEQ ID NO: 23) | 106 | C->A | no | CCG-C-AAG | CCG-A-AAG | no |
| GTGTCCCACCCACCCACCC (SEQ ID NO: 24) | 83 | A->G | yes | ACA-A-CTG | ACA-G-CTG | no |
| TCCCAGGCAGCTACCCGCA (SEQ ID NO: 25) | 102 | T->C | yes | GCG-T-CCC | GCG-C-CCC | yes |
| TGACGCGCCGGTTGGGCCC (SEQ ID NO: 26) | 106 | A->C | no | ACC-A-CCT | ACC-C-CCT | yes |

Table 1 indicates discrepancies between designed and read library. Each error is one row, displaying the barcode the error is associated with, the position in the oligo (out of 115), the error type, whether or not the error resulted in a bit change, the original context, and the new context (error position is in the middle of dashes), and finally whether or not the error resulted in a run of 4 bases that could have been filtered out. Lines that resulted in bit errors are bolded, and lines that could have been filtered based on runs of 4 consecutive bases are shaded.

EXAMPLE VI

Calculations on Data Density

Theoretical DNA density was calculated by using 2 bits per nucleotide of single stranded DNA. The molecular weight of DNA we used was based on an average of 330.95 g/mol/nucleotide of anhydrous weight for the sodium salt of an ATGC balanced library. This results in a weight density of 1 bit per $2.75 \times 10^{-22}$ g, and thus $1.8 \times 10^{21}$ bytes can be stored in 3.96 g. Of course, practical maximums would be several orders of magnitude less dense depending the types of redundancy, barcoding, and encoding schemes desired. This theoretical maximum calculation is not used in FIG. 1B.

Figure 1B:
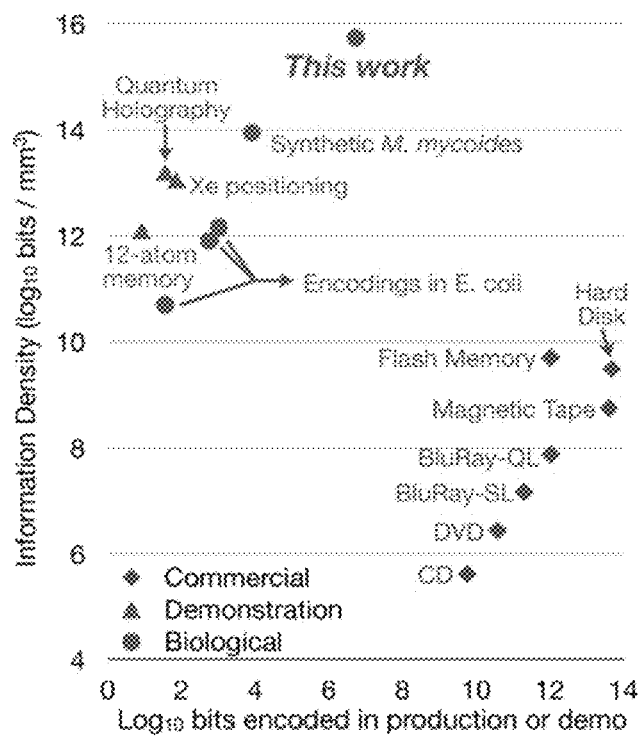
FIG. 1B is a graphical comparison to other technologies. We plotted information density ($\log_{10}$ of bits/mm$^3$) versus current scalability as measured by the logio of bits encoded in the report or commercial unit See 4. Information on materials and methods is available on Science Online.

Data plotted on FIG. 1B is a comparison between very different technologies. In cases of planar density calculations where thickness was not reported, 100 μm was chosen as depth (this is ~10× smaller than a hard drive platter, and 33% smaller than current Flash memory stacking). Current information encoding density (96 bits per 159 bp), and 100× synthesized coverage of the DNA in storage was assumed. An approximate volume of 1 g/cm³, the density of pure water, which is probably a slight underestimate for dry DNA was assumed.

TABLE 2

| Type | Label | Date | Ref | Bits | Bits/mm3 | Comments |
|---|---|---|---|---|---|---|
| Commercial | CD | 1982 | (19) | 5.6e9 | 4.13e5 | 1.2 mm thick CD; 120 mm diameter |
| Commercial | DVD-SL | 1996 | (20) | 3.76e10 | 2.77e6 | 1.2 mm thick DVD-SS-SL; 120 mm diameter |
| Commercial | DVD-QL | 2000 | (20) | 1.37e11 | 1.01e7 | 1.2 mm thick DVD-DS-DL; 120 mm diamter |
| Commercial | BluRay SL | 2002 | (21) | 2.00e11 | 1.47e7 | 1.2 mm thick Blu-ray disk (1 layer) |
| Commercial | BluRay QL | 2010 | (21) | 1.02e12 | 7.52e7 | 1.2 mm thick Blu-ray disk (XL 4 layer) |
| Commercial | Magenetic Tape | 2010 | (22) | 4.00e13 | 5.59e8 | Oracle StorageTek T10000 T2 - 5TB 5.2 μm thickness, 1147 m length, ~12 mm wide |

TABLE 2-continued

| Type | Label | Date | Ref | Bits | Bits/mm3 | Comments |
|---|---|---|---|---|---|---|
| Commercial | Flash Memory | 2012 | (23, 24) | 1.02e12 | 5.02e9 | NAND Flash; Sandisk for density of a single chip (22) 128 Gbits in 170 mm2; 150 μm depth taken from Toshiba chip stacking (23) |
| Commercial | Hard Disk | 2012 | (25) | 4.80e13 | 3.10e9 | Hard Drive -> Seagate 1 Terabit/inch2 = 1.55e9 bits/mm2 = 1.55e9 bits/mm2 assuming ds1 mm platter |
| Demonstration | 12-atom memory | 2012 | (26) | 8 | 1.11e12 | 9 nm2/bit (assuming 100 μm thickness) low temperature non-volatile memory |
| Demonstration | Xe positioning | 1991 | (27) | 70 | 1E13 | Spelled IBM with Xe atoms spaced 1 nm apart on a 14 × 5 nm¬2 lattice; 1 bit/nm2; assuming 100 μm thickness |
| Demonstration | Quantum Holography | 2008 | (28) | 3.5E+1 | 1.38e13 | 35 bit image pair, 17 × 17 nm2 overhead atoms and 4 × 5 read space = ((4 × 5)/(17 × 17)) * 20 bits/nm2 = 1.38 bits/nm2 = 1.38e12 bits/mm2; assuming 100 μm thickness |
| Biological | Super-resolution GFP | 2011 | (29) | 27 | 4.0E10 | 9 3 × 3 bit fields (81 bits); 250 nm center-to-center spacing; 1 bit/250 nm2; assuming 100 μm thickness |
| Biological | DNA in E. coli | 1988 | (7, 30) | 35 | 5.0e10 | E. coli, 0.7 μm3 from (29) |
| Biological | DNA in E. coli | 2001 | (3, 30) | 561 | 8.01e11 | E. coli 0.7 μm3 - 118 characters (27 possibilities) = 27118 = 2x; x = 561 |
| Biological | DNA in E. coli | 2005 | (8, 30) | 1007 | 1.44e12 | E. coli, 0.7 □m3 - 233 characters (20 possibilities) = 20233 = 2x; x = 1007 |
| Biological | Mycoplasma | 2010 | (9) | 7920 | 8.80E+13 | Mycoplasma, volume of ~0.09 μm3; |
| Biological | This Work | 2012 | | 5.27e6 | 5.49e15 | Assuming 1e-3 g/mm3; 330.95 g/mol/nucleotide; 96 bits per 159 bp; 100x fold coverage; 330.95*2*159 = 105242.1 g/mol = 1.748e-19 g/molecule = 1.748e-16 g per 1000 molecules = 1.748e-13 mm3 |

Table 2 shows data used in FIG. 1B to compare data densities in different media. In order to compare vastly different technologies for information encoding, all data density information was converted into volumetric data densities by making various assumptions. For commercial technologies, available information was used about substrate thickness where available. In the case of flash memory, best in class data density was combined with chip-stacking thickness from different manufacturers. For demonstration data storage technologies, substrate thicknesses were not reported. Therefore 100 μm thickness was assumed, which is $\frac{1}{3}^{rd}$ the current thickness of stacked flash storage technologies. This may be unrealistic for those technologies as published as all the demonstrations were performed at 4° K and in vacuum. The density of dried DNA was approximated to water's density, which may be an underestimation. For other biological demonstrations using cloned DNA, volumes of individual cells was used as volume. Finally, greyed rows are not shown in FIG. 1B as they were obscured by other data points, but are included here for completeness.

EXAMPLE VII

Code

```
Bits2DNA.pl
# cd "\Perl\gmc\Bin_DNA"
# \Perl\bin\perl Bits2DNA.pl GMC Jul-2011 & 27-May-2012
# docstore.mik.ua/orelly/perl/cookbook/ch02_05.htm
  (bin) ch01_05.htm (char)
# http://perldoc.perl.org/functions/pack.html rand.html
# Each oligo is L(19)+8N(12)= 115 bp, long flanked by
  22-mer amplification primers.
```

| Code |
|---|
| ```
#DNA Encoded Artifacts Registry (DEAR) to coordinate global standards.
open IN,"in.html"; open OUT,">Bits2DNA.txt"; binmode IN;
$t{"0"}="a"; $t{"1"}="G"; # lowercase a,c = zero bit.
$t{"a"}="c"; $t{"G"}="T"; $t{"c"}="a"; $t{"T"}="G";
$u1=""; $u2=""; $u3=""; # Initialize; keep homopolymer runs <4
$N=12; # Length of segment in bytes (not including segment number)
$L=19; # 2^19 = 524,288 = max number of oligos L=00010011
$seed=2; srand($seed); # remove this line to get a random seed
print int2bp(262144)," ",int2bp(262145);
$f="CTACACGACGCTCTTCCGATCT"; # forward 'universal'
sequencing & amplification primer (SEQ ID NO:27)
$r="AGATCGGAAGAGCGGTTCAGCA"; # reverse 22-mer
primer (SEQ ID NO:28)
$n=0; print OUT $f,int2bp(0),""; ###
while (read (IN, $text, 65536)) {
        @ascii_num = unpack("C*", $text);
    foreach $val (@ ascii_num) {
        print OUT byt2bp($val); ###
        $n++;
        if($n%$N==0){
           print OUT $r,"\n",$f,int2bp($n/$N),""; ###
        } # N bases per output line
    } # each byte
} # 65 Kbytes
for ($k=$n%$N; $k<$N; $k++){
    print OUT byt2bp(int(rand(256))); ###
} # pad last data line to keep all oligos same size.
    print OUT "$r\n"; ###
sub byt2bp { # convert rightmost 8 bits (MSB first byte) to 8 bp
    my $b = unpack("B32", pack("N", shift));
    $p="";
    for ($i=24; $i<=31; $i++){
        $x=substr($b,$i,1); # bits 24 to 31 inclusive
        $u=$t{$x};
        if(rand(2)<1){$u=$t{$u};} # pick synonym a=c; G=T
        if(($u eq $u1) && ($u eq $u2) && ($u eq $u3)){$u=$t{$u};}
        $u1=$u2; $u2=$u3; $u3=$u; # Shift previous base string
        $p = $p.$u;
    }
    return $p;
}
sub int2bp { # convert rightmost $L bits of 32 bit integers to $L bp
    my $b = unpack("B32", pack("N", shift));
    $p="";
    for ($i=31; $i>=32-$L; $i--){
        $x=substr($b,$i,1); # bits 31 to $L
        $u=$t{$x};
        if(rand(2)<1){$u=$t{$u};} # pick synonym a=c; G=T
        if(($u eq $u1) && ($u eq $u2) && ($u eq $u3)){$u=$t{$u};}
        $u1=$u2; $u2=$u3; $u3=$u; # Shift previous base string
        $p = $p.$u;
    }
    return $p;
}
buildConsensus.py
import sys
#builds consensus sequence from individual base counts
def getConsensus(finalbuckets):
    sequence = ''
    for i in range(len(finalbuckets)):
        letterindex = finalbuckets[i].index(max(finalbuckets[i]))
        if letterindex == 0:
            sequence += 'A'
        elif letterindex == 1:
            sequence += 'C'
        elif letterindex == 2:
            sequence += 'G'
        elif letterindex == 3:
            sequence += 'T'
    return sequence
oligolength = 115
currentbarcode = ''
#initialize vector to building consensus
buckets = [[0 for col in range(4)]for row in range(oligolength)]
for line in sys.stdin:
    splitline = line.split( )
    count = int(splitline[0])
``` |

| Code |
|---|
| ```
    barcode = splitline[1]
    sequence = splitline[2]
    if not barcode == currentbarcode:
        if not currentbarcode =='':
            print getConsensus(buckets)
        buckets = [[0 for col in range(4)] for row in range(oligolength)]
        currentbarcode = barcode
    for i in range(oligolength):
        if sequence[i] == 'A':
            buckets[i][0] += count
        elif sequence[i] == 'C':
            buckets[i][1] += count
        elif sequence[i] == 'G':
            buckets[i][2] += count
        elif sequence[i] == 'T':
            buckets[i][3] += count
#print final consensus
print getConsensus(buckets)
``` |

EXAMPLE VIII

Process Summary

According to one aspect, html-coded draft of a book that included 53,426 words, 11 JPG images and 1 Javascript program was converted into 5.27 megabits See 4. Information on materials and methods is available on Science Online. The bits were then encoded onto 54,898 159 nt oligonucleotides each encoding a 96-bit data block (96 nt), a 19-bit address specifying the location of the data block in the bit stream (19 nt), and flanking 22 nt common sequences for amplification and sequencing. The oligonucleotide library was synthesized by ink-jet printed, high-fidelity DNA microchips See 10. E. M. LeProust et al., Nucleic Acids Research 38, 2522-2540 (2010). To read the encoded book, the library was amplified by limited-cycle PCR and then sequenced on a single lane of an Illumina HiSeq. Overlapping paired-end 100 nt reads were joined to reduce the effect of sequencing error See 11. J. St. John, SeqPrep https://github.com/jstjohn/SeqPrep (2011). Then using only reads that gave the expected 115 nt length and perfect barcode sequences, consensus was generated at each base of each data block at an average of about 3000-fold coverage. All data blocks were recovered with a total of 10 bit errors (out of 5.27 million), which were predominantly located within homo-polymer runs at the end of the oligo where we only had single sequence coverage See 4. Information on materials and methods is available on Science Online.

The density of the embodiments disclosed herein was about 5.5 petabits/mm$^3$ at 100× synthetic coverage. The scale of the embodiments disclosed herein was about 5.27 megabits. The method steps described herein were carried out using commercially available materials and instruments. FIG. 1B is a comparison of information density showing that the embodiments of the present disclosure ("This work") provided a higher information density compared with other storage media. According to certain aspects, embodiments include the use of compression, redundant encodings, parity checks, and error correction to improve density, distribution, and error rate. According to certain aspects, DNA libraries can also be stored without physical isolation by using unique priming sites that allow for orthogonal amplification See 12. S. Kosuri et al., Nature Biotechnology 28, 1295-1299 (2010). According to certain aspects, polymers other than DNA or DNA modifications can also be used to maximize reading, writing, and storage capabilities See 13. S. A. Benner, Z. Yang, F. Chen, Comptes Rendus Chimie 14, 372-387 (2011). According to one aspect, a hand-held, single-molecule DNA sequencer may be used to read DNA-encoded information See 15. E. Pennissi, Science 336, 534-537 (2012). According to one aspect, the general approach of using addressed data blocks combined with library synthesis and consensus sequencing is compatible with commercially available DNA sequencing and synthesis technologies. According to one aspect, alternative consumer-level uses of DNA such as information storage could accelerate development of new technologies for improving synthesis and sequencing technologies See 16. S. Kosuri, A. M. Sismour, ACS Synth Biol 1, 109-110 (2012).

References identified herein and the following references are hereby incorporated by reference in their entireties for all purposes and are referred to throughout the present disclosure by the corresponding number.

1. "Extracting Value from Chaos" (IDC, Framingham, MA 2011); world wide web site emc.com/collateral/analyst-reports/idc-extracting-value-from-chaos-ar.pdf.
2. J. Rothenberg, *Scientific American* 272, 42-47 (1995).
3. C. Bancroft, T. Bowler, B. Bloom, C. T. Clelland, *Science* 293, 1763-1765 (2001).
4. Information on materials and methods is available on Science Online
5. J. Bonnet et al., *Nucleic Acids Research* 38, 1531-1546 (2010).
6. S. Pääbo et al., M. A. Uyterlinde et al., Eds. *Annual Review of Genetics* 38, 645-679 (2004).
7. J. Davis, *Art Journal* 55, 70-74 (1996).
8. C. Gustafsson, *Nature* 458, 703 (2009).
9. D. G. Gibson et al., *Science* 329, 52-56 (2010).
10. E. M. LeProust et al., *Nucleic Acids Research* 38, 2522-2540 (2010).
11. J. St. John, *SeqPrep* https://github.com/jstjohn/SeqPrep (2011)
12. S. Kosuri et al., *Nature Biotechnology* 28, 1295-1299 (2010).
13. S. A. Benner, Z. Yang, F. Chen, *Comptes Rendus Chimie* 14, 372-387 (2011).
14. P. A. Carr, G. M. Church, *Nature Biotechnology* 27, 1151-62 (2009).
15. E. Pennissi, *Science* 336, 534-537 (2012)
16. S. Kosuri, A. M. Sismour, *ACS Synth Biol* 1, 109-110 (2012)
17. B. Langmead, S. L. Salzberg, *Nature Methods* 9, 357-360 (2012).
18. H. Li et al., *Bioinformatics* 25, 2078-2079 (2009).
19. Ecma International, *Data interchange on read-only 120 mm optical data disks* (CD-ROM), (ECMA Standard 130, Geneva, Switzerland 1996, world wide website ecma-international.org/publications/files/ECMA-ST/Ecma-130.pdf.)
20. Ecma International, *120 mm DVD-Read-Only Disk*, (ECMA Standard 267, Geneva, Switzerland 2001, world wide website ecma-international.org/publications/files/ECMA-ST/Ecma-267.pdf.)
21. Blu-Ray Disc Association, *White Paper—Blu-Ray Disc Format* (2$^{nd}$ Edition, Universal City, CA 2010, world wide website blu-raydisc.com/Assets/Downloadablefile/general bluraydiscformat-15263.pdf.)
22. *Oracle, StorageTek T10000 Family Tape* Cartridge (Oracle, Redwood Shores, CA 2010, world wide website oracle.com/us/products/servers-storage/storage/tape-storage/033617.pdf.)
23. SanDisk, *SanDisk Develops Smallest 128Gb NAND Flash Memory Chip* (SanDisk, Milipitas, CA 2012, world wide website www.sandisk.com/about-sandisk/press-room/press-releases/2012/sandisk-develops-worlds-smallest-128gb-nand-flash-memory-chip.)
24. Toshiba, *NAND Flash Memory in Multi Chip Package* (Toshiba, Tokyo, Japan, 2011, world wide website toshiba-components.com/memory/mcp.html.)
25. Seagate, *Seagate Reaches 1 Terabit Per Square Inch Milestone In Hard Drive Storage With New Technology Demonstration* (Seagate, Cupertino, CA 2012, world wide website seagate.com/about/newsroom/press-releases/terabit-milestone-storage-seagate-pr/?param ChannelName=newsroom.)
26. S. Loth et al., *Science* 335, 196-199 (2010).
27. D. M. Eigler, E. K. Schweizer, *Nature* 344, 524-526 (1990).
28. C. R. Moon, L. S. Mattos, B. K. Foster, G. Zeltzer, H. C. Manoharan, *Nature Nanotechnology* 4, 167-172 (2009).
29. T. Grotjohann et al., *Nature* 478, 204-208 (2011).
30. H. E. Kubitschek, *J Bacteriol* 172, 94-101 (1990).
31. "Screening Framework Guidance for Providers of Synthetic Double-Stranded DNA" Federal Registrar 75, 62820-62832 (2010) FR Doc No: 2010-25728.

EQUIVALENTS

Other embodiments will be evident to those of skill in the art. It should be understood that the foregoing description is provided for clarity only and is merely exemplary. The spirit and scope of the present invention are not limited to the above example, but are encompassed by the claims. All publications, patents and patent applications cited above are incorporated by reference herein in their entirety for all purposes to the same extent as if each individual publication or patent application were specifically indicated to be so incorporated by reference.

What is claimed is:

1. A method of synthesizing de novo a polynucleotide comprising
synthesizing de novo a known polynucleotide using a programmable template independent polymerase to incorporate particular dNTPs to form the known polynucleotide.

2. The method of claim 1 wherein the known polynucleotide is a naturally occurring polynucleotide.

3. The method of claim 1 wherein the known polynucleotide is a synthetic polynucleotide.

4. The method of claim 1 wherein the step of synthesizing comprises
using a cyclic pattern of dNTP solutions and the template independent polymerase to incorporate the dNTPs.

5. The method of claim 1 wherein the template independent polymerase is terminal deoxynucleotidyl transferase or poly(A) polymerase.

6. The method of claim 1 wherein the polymerase function of the template independent polymerase is programmable by light.

7. The method of claim 1 wherein the base-specificity of the template independent polymerase is programmable by light.

8. The method of claim 1 wherein the known polynucleotide is synthesized on a support.

9. The method of claim 8 wherein the support is a solid or semi-solid support.

10. The method of claim 8 wherein the support comprises spatially defined sites.

11. The method of claim 8 wherein the support comprises spatially defined addressable sites.

12. The method of claim 8 wherein the support is a member selected from the group consisting of a slide, bead, chip, particle, strand, gel, sheet, tubing, sphere, container, capillary, pad, slice, film, and plate.

13. The method of claim 8 wherein the support is a substantially planar support comprising trenches, grooves, wells or chemical barriers.

14. The method of claim 8 wherein the known polynucleotide is covalently attached to the support.

15. The method of claim 8 wherein the known polynucleotide is attached to the support with a cleavable linker.

16. The method of claim 8 wherein the known polynucleotide is synthesized on the support using ink jet techniques.

17. The method of claim 8 wherein the known polynucleotide is synthesized on the support using electrochemical techniques.

18. The method of claim 8 wherein the known polynucleotide is synthesized on the support using microfluidic techniques.

* * * * *

SEQUENCE LISTING

```
Sequence total quantity: 28
SEQ ID NO: 1            moltype = DNA   length = 33
FEATURE                 Location/Qualifiers
misc_feature            1..33
                        note = MD Test 1-F Primer
source                  1..33
                        mol_type = other DNA
                        organism = synthetic construct
SEQUENCE: 1
acactctttc cctacacgac gctcttccga tct                                33
```

```
SEQ ID NO: 2                moltype = DNA   length = 33
FEATURE                     Location/Qualifiers
misc_feature                1..33
                            note = MD Test 1-R Primer
source                      1..33
                            mol_type = other DNA
                            organism = synthetic construct
SEQUENCE: 2
ctcggcattc ctgctgaacc gctcttccga tct                                    33

SEQ ID NO: 3                moltype = DNA   length = 58
FEATURE                     Location/Qualifiers
misc_feature                1..58
                            note = PE PCR Primer 1.0 - F
source                      1..58
                            mol_type = other DNA
                            organism = synthetic construct
SEQUENCE: 3
aatgatacgg cgaccaccga gatctacact ctttccctac acgacgctct tccgatct         58

SEQ ID NO: 4                moltype = DNA   length = 61
FEATURE                     Location/Qualifiers
misc_feature                1..61
                            note = PE PCR Primer 2.0 - R
source                      1..61
                            mol_type = other DNA
                            organism = synthetic construct
SEQUENCE: 4
caagcagaag acggcatacg agatcggtct cggcattcct gctgaaccgc tcttccgatc       60
t                                                                       61

SEQ ID NO: 5                moltype = DNA   length = 19
FEATURE                     Location/Qualifiers
misc_feature                1..19
                            note = Synthesized Barcode
source                      1..19
                            mol_type = other DNA
                            organism = synthetic construct
SEQUENCE: 5
aactgtcgct attcactca                                                    19

SEQ ID NO: 6                moltype = DNA   length = 19
FEATURE                     Location/Qualifiers
misc_feature                1..19
                            note = Synthesized Barcode
source                      1..19
                            mol_type = other DNA
                            organism = synthetic construct
SEQUENCE: 6
actaacgcac ctggaatca                                                    19

SEQ ID NO: 7                moltype = DNA   length = 19
FEATURE                     Location/Qualifiers
misc_feature                1..19
                            note = Synthesized Barcode
source                      1..19
                            mol_type = other DNA
                            organism = synthetic construct
SEQUENCE: 7
actttcggca tgagtaccc                                                    19

SEQ ID NO: 8                moltype = DNA   length = 19
FEATURE                     Location/Qualifiers
misc_feature                1..19
                            note = Synthesized Barcode
source                      1..19
                            mol_type = other DNA
                            organism = synthetic construct
SEQUENCE: 8
agcggctcgt cggtgtccc                                                    19

SEQ ID NO: 9                moltype = DNA   length = 19
FEATURE                     Location/Qualifiers
misc_feature                1..19
                            note = Synthesized Barcode
source                      1..19
                            mol_type = other DNA
                            organism = synthetic construct
```

```
SEQUENCE: 9
atacggctca ttacaaacc                                                    19

SEQ ID NO: 10           moltype = DNA   length = 19
FEATURE                 Location/Qualifiers
misc_feature            1..19
                        note = Synthesized Barcode
source                  1..19
                        mol_type = other DNA
                        organism = synthetic construct
SEQUENCE: 10
atgcgggcaa atcacagca                                                    19

SEQ ID NO: 11           moltype = DNA   length = 19
FEATURE                 Location/Qualifiers
misc_feature            1..19
                        note = Synthesized Barcode
source                  1..19
                        mol_type = other DNA
                        organism = synthetic construct
SEQUENCE: 11
atggccgtaa tggagaaac                                                    19

SEQ ID NO: 12           moltype = DNA   length = 19
FEATURE                 Location/Qualifiers
misc_feature            1..19
                        note = Synthesized Barcode
source                  1..19
                        mol_type = other DNA
                        organism = synthetic construct
SEQUENCE: 12
atgttctgaa ttagcgccc                                                    19

SEQ ID NO: 13           moltype = DNA   length = 19
FEATURE                 Location/Qualifiers
misc_feature            1..19
                        note = Synthesized Barcode
source                  1..19
                        mol_type = other DNA
                        organism = synthetic construct
SEQUENCE: 13
caatgtagat cctcgaaac                                                    19

SEQ ID NO: 14           moltype = DNA   length = 19
FEATURE                 Location/Qualifiers
misc_feature            1..19
                        note = Synthesized Barcode
source                  1..19
                        mol_type = other DNA
                        organism = synthetic construct
SEQUENCE: 14
ccggcctaaa cggcacgcc                                                    19

SEQ ID NO: 15           moltype = DNA   length = 19
FEATURE                 Location/Qualifiers
misc_feature            1..19
                        note = Synthesized Barcode
source                  1..19
                        mol_type = other DNA
                        organism = synthetic construct
SEQUENCE: 15
cgatattcgg gaacaccca                                                    19

SEQ ID NO: 16           moltype = DNA   length = 19
FEATURE                 Location/Qualifiers
misc_feature            1..19
                        note = Synthesized Barcode
source                  1..19
                        mol_type = other DNA
                        organism = synthetic construct
SEQUENCE: 16
cgatattcgg gaacaccca                                                    19
```

```
SEQ ID NO: 17           moltype = DNA  length = 19
FEATURE                 Location/Qualifiers
misc_feature            1..19
                        note = Synthesized Barcode
source                  1..19
                        mol_type = other DNA
                        organism = synthetic construct
SEQUENCE: 17
cggcggagcg gagacgcca                                                19

SEQ ID NO: 18           moltype = DNA  length = 19
FEATURE                 Location/Qualifiers
misc_feature            1..19
                        note = Synthesized Barcode
source                  1..19
                        mol_type = other DNA
                        organism = synthetic construct
SEQUENCE: 18
ctgctcttca accgctaca                                                19

SEQ ID NO: 19           moltype = DNA  length = 19
FEATURE                 Location/Qualifiers
misc_feature            1..19
                        note = Synthesized Barcode
source                  1..19
                        mol_type = other DNA
                        organism = synthetic construct
SEQUENCE: 19
ggtaatttct agtacagcc                                                19

SEQ ID NO: 20           moltype = DNA  length = 19
FEATURE                 Location/Qualifiers
misc_feature            1..19
                        note = Synthesized Barcode
source                  1..19
                        mol_type = other DNA
                        organism = synthetic construct
SEQUENCE: 20
ggtcgcataa acttgaccc                                                19

SEQ ID NO: 21           moltype = DNA  length = 19
FEATURE                 Location/Qualifiers
misc_feature            1..19
                        note = Synthesized Barcode
source                  1..19
                        mol_type = other DNA
                        organism = synthetic construct
SEQUENCE: 21
ggtcgcataa acttgaccc                                                19

SEQ ID NO: 22           moltype = DNA  length = 19
FEATURE                 Location/Qualifiers
misc_feature            1..19
                        note = Synthesized Barcode
source                  1..19
                        mol_type = other DNA
                        organism = synthetic construct
SEQUENCE: 22
gtgccaataa agtggtccc                                                19

SEQ ID NO: 23           moltype = DNA  length = 19
FEATURE                 Location/Qualifiers
misc_feature            1..19
                        note = Synthesized Barcode
source                  1..19
                        mol_type = other DNA
                        organism = synthetic construct
SEQUENCE: 23
gtgccaataa agtggtccc                                                19

SEQ ID NO: 24           moltype = DNA  length = 19
FEATURE                 Location/Qualifiers
misc_feature            1..19
                        note = Synthesized Barcode
source                  1..19
                        mol_type = other DNA
                        organism = synthetic construct
```

```
SEQUENCE: 24
gtgtcccacc cacccaccc                                                          19

SEQ ID NO: 25           moltype = DNA  length = 19
FEATURE                 Location/Qualifiers
misc_feature            1..19
                        note = Synthesized Barcode
source                  1..19
                        mol_type = other DNA
                        organism = synthetic construct
SEQUENCE: 25
tcccaggcag ctacccgca                                                          19

SEQ ID NO: 26           moltype = DNA  length = 19
FEATURE                 Location/Qualifiers
misc_feature            1..19
                        note = Synthesized Barcode
source                  1..19
                        mol_type = other DNA
                        organism = synthetic construct
SEQUENCE: 26
tgacgcgccg gttgggccc                                                          19

SEQ ID NO: 27           moltype = DNA  length = 22
FEATURE                 Location/Qualifiers
misc_feature            1..22
                        note = Computer code forward universal sequencing and
                         amplification primer
source                  1..22
                        mol_type = other DNA
                        organism = synthetic construct
SEQUENCE: 27
ctacacgacg ctcttccgat ct                                                      22

SEQ ID NO: 28           moltype = DNA  length = 22
FEATURE                 Location/Qualifiers
misc_feature            1..22
                        note = Reverse 22-mer primer
source                  1..22
                        mol_type = other DNA
                        organism = synthetic construct
SEQUENCE: 28
agatcggaag agcggttcag ca                                                      22
```